Nov. 27, 1945. M. M. GRAHAM Plant Pat. 662
AVOCADO TREE
Filed Nov. 14, 1944
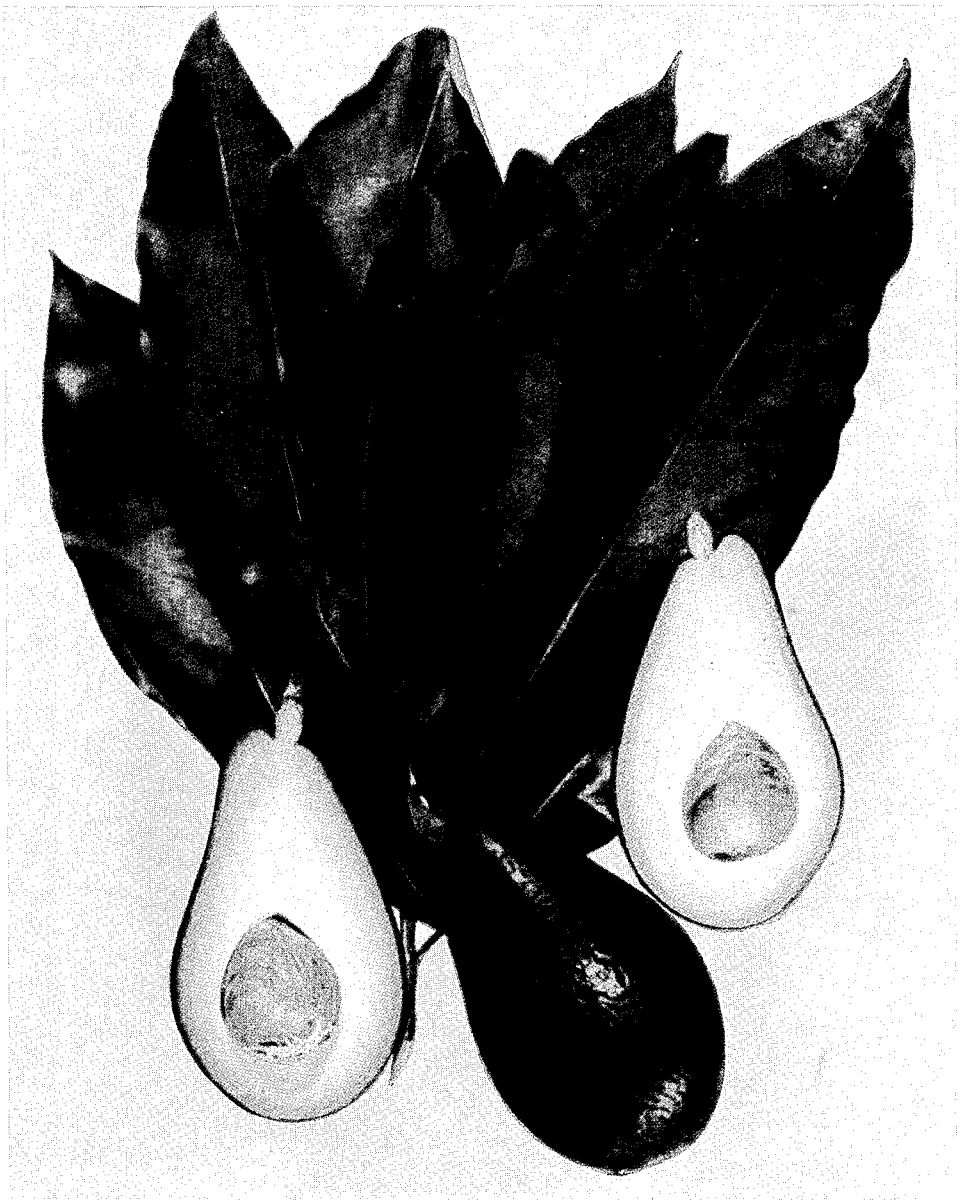
Inventor
M. M. Graham
By Robb & Robb
His Attorneys.

Patented Nov. 27, 1945

Plant Pat. 662

UNITED STATES PATENT OFFICE

662

AVOCADO TREE

Melville M. Graham, La Habra, Calif., assignor to Armstrong Nurseries, Inc., Ontario, Calif., a corporation of California Application November 14, 1944, Serial No. 563,358

1 Claim. (Cl. 47—62)

The present discovery relates to a new and distinct variety of avocado plant, representing a marked improvement not only upon its parent but also with respect to those varieties well known in the section where the new variety originated. It belongs to the group known as the Guatemalan type, having no noticeable anise content in the leaves, with only moderate to slight resistance to frost.

The new variety originated by the planting by me of a seed of a Lyon avocado tree which had been open pollinated. In the care and development of the seedling, observations of its habits and other characteristics disclosed many points of novelty and distinction, and asexual reproduction has proved these characteristics to be established.

This new avocado is a slender, upright tree resembling somewhat the variety Lyon, but it is distinguishable from that variety in that its leaves are longer and broader, and there is a tendency for it to hold the lower branches better than Lyon and on maturity to reach a greater spread than its parent variety. The tree further differs from Lyon in being more easily propagated by budding, the Lyon being notably difficult to propagate by this method.

The present variety is further characterized as to novelty by a blooming date six to eight weeks later than the Fuerte variety in the area of its origin, the dates of normal maturity running between April 1st and June 1st, but uniquely it maintains many fruit on the tree, if not picked, as late as September 1st.

Further distinguishing, it bears fruits of higher quality in both flavor and oil content than Lyon, said fruits resembling those of the latter somewhat as to shape, but they are usually slightly shorter and broader in outline, and far superior in keeping qualities as evidenced by the fact that they keep as much as two weeks when cut hard and allowed to ripen in room temperature of about 70° F. This ability to ripen when cut in a hard state without spoiling, makes it different from any other variety known to me and more importantly, its habit of sealing over the cut surface when soft-ripe fruits are cut, allowing the portion untouched by the knife to remain in edible condition for several days, makes it further outstanding in respect to this keeping quality.

The fruits ripen evenly with relatively high oil content, with a distinct nut-like aroma, uniform but asymmetrical and pyriform with an oblique base and the apex broadly rounded, sometimes with a slight depression at one side of the pistil point. It characteristically ripens evenly, contains few fine fibers, is of fine texture, nutty rich flavor, free from sweetness, bitterness or soapiness. The keeping quality is outstanding again, in that it does not lose flavor after cutting as do most varieties of avocado. Fruits are characteristically variable in size, being between medium and large as compared to other varieties, with an average weight between 16 and 18 ounces, but varying from 11 ounces to 29 ounces in the extremes.

The seed in relation to the fruit is of relatively small size, usually averaging between 12% and 15% of the total weight of the fruit. It is characteristically broadly ovate, with a broadly rounded base sometimes somewhat flat, with an obtuse apex.

The following is a detailed description of the new variety based upon observations of specimens grown at La Habra, California, color terminology being in accord with Ridgway's Color Standard:

Dates of first and last picking: April 1st to June 1st when picked at proper stage for marketing, but many fruits may be left on tree until September 1st and still retain high degree of edibility and quality.

Tree: Medium to small, slender upright, fairly dense; tender to frost with respect to Mexican avocado varieties; productive; alternates between medium heavy and light medium crops.

*Trunk.*—Medium to slender.

*Branches.*—Medium to slender; fairly smooth with scattered lenticels varying in size and shape. *Color*—near and varying from Lime Green, Plate XXXI; tender terminal growth, near Rinman's Green, Plate XVIII; newly hardened terminal growth, near Absinthe Green, Plate XXXI. *Pubescence*—slight on tender terminal growth.

*Leaves.*—*Length*—variable up 14 inches. *Width*—variable up to 7 inches. Large, medium to thin; ovate-lanceolate, usually broadly cuneate at base, sometimes varying to slightly rounded at base. *Color of mature leaf*—upper side: between Danube Green, Plate XXXII, and Ivy Green, Plate XXXI; under side: between Sage Green, Plate XLVII, and Pistachio Green, Plate XLI. Net veins, near Pois Green, Plate XLI; larger veins, near Light Turtle Green, Plate XXXII, becoming lighter toward margin to near Pois Green, Plate XLI; midrib, near Absinthe Green, Plate XXXI, becoming somewhat lighter toward apex. Margin of leaf is very near Absinthe Green, Plate XXXI. Freshly torn leaf does not have Anise smell. New leaf: 3 to 4 inches long. Color, upper side, near Olive Brown, Plate XL; under side, near Light Elm Green, Plate XVII. *Petiole*—Medium long; medium thick. Grooved on upper side only. Color, near Deep Dull Yellow, Plate XXXII, at base, becoming lighter toward leaf.

*Flower-Buds.*—Moderately large.

*Flowers.*—Moderately large; blooms six to eight weeks later than Fuerte in the La Habra district. Blooming dates vary depending upon seasons.

Fruit: Maturity when described—ripe, proper stage for eating. Date—August 30, 1944, at end of ripening season.

*Size.*—Variable; medium to large. Dameter axial—5 to 6½ inches. Maximum transverse diameter—3 to 4 inches. Weight—11¼ ounces to 29 ounces. Average fruit 16 to 18 ounces.

*Form.*—Uniform, asymmetrical, pyriform. *Base*—slightly umbilicate; oblique. *Apex*—Broadly rounded, sometimes slightly depressed at one side of pistil point. *Stem*—length—3 to 4 inches. Medium stout; glabrous. Color—near and varying from Cedar Green, Plate VI.

*Skin.*—Medium thin for Guatemalan type; tender to medium tough; slightly tenacious to flesh; moderately smooth. Tendency to crack—none. Color of skin of mature fruit first ready to eat, between and varying from Dark Dull Yellow, Plate XXXII, to Cerro Green, Plate V. Skin surface dotted with small flecks or dots of near Absinthe Green, Plate XXXI, and somewhat larger woody dots of between Army Brown, Plate XL, and Cinnamon Drab, Plate XLVI. Brown dots more numerous on largest diameter of fruit, becoming less numerous toward the apex and base.

*Flesh.*—*Color*—region next to skin (approximately ¼ inch) between Cirvette Green, Plate XVIII, and Bice Green, Plate XXI, blending sharply toward the pit cavity to between Deep Colonial Buff, Plate XXX, and Chartreuse Yellow, Plate XXXI. Surface of flesh on cut fruit shows scattered small fibers of between Buffy Brown, Plate XI, and Dark Olive Buff, Plate XL. Few fibers near and parallel to green region near skin are between Seafoam Yellow, Plate XXXI, and Chartreuse Yellow, Plate XXXI. Surface of seed cavity, near and varying from Pale Dull Green Yellow, Plate XVII. *Texture* — fine. *Fibers* — few; fine. *Ripens*—evenly; maturity season, April to August, inclusive. *Flavor*—superior; nutty; rich; free from sweetness, bitterness, and soapiness. *Aroma*—distinct and nut-like.

Eating quality: Excellent.

Shipping qualities: Good.

Keeping quality: Fruit has excellent keeping qualities, making a coating over the cut surface which dries and retains the moisture of the fruit in fine condition for a long time. Fruit does not lose flavor after cutting as do some varieties.

Yield: Medium to heavy, depending upon the age of the tree.

Oil content: From 17.85% in February increasing as the season advances to 26.59% in August.

Seed:

*Size.*—Small to medium, relative to size of fruit. Breadth — 1¾ to 2 inches. Length—2 to 2½ inches. Weight—2 to 2½ ounces for fruits weighing about 16 ounces.

*Form.*—Broadly ovate, symmetrical. Base—Broadly rounded to flattened. Hilium—broad. Apex—obtuse. Sides—equal. Seed germinating and split when taken from fruit when described at end of ripening season.

*Surface.*—Rough. Seed coat adheres to seed when removed from ripened fruit.

*Color of seed surface (seed coat removed).*—Between Onion Skin Pink, Plate XXVII, and Vinaceous Cinnamon, Plate XXIX, shading to near Pale Pinkish Cinnamon, Plate XXIX, at base. Surface is dotted with and irregular line indentations are colored with near Orange Cinnamon, Plate XXIX.

I claim:

A new and distinct variety of Avocado tree, characterized as to novelty by its slender, upright, spreading habit of growth; size and shape of its foliage; easiness of propagation by budding in comparison with its parent variety; lateness of blooming and ability to maintain many fruit thereon long after the period of maturity; the production of fruit superior in both flavor, oil content, and keeping quality; the ability of the fruit to ripen when cut hard without spoiling, to seal over the cut surface when cut at soft-ripe stage and remain in edible condition thereafter; the habit of fruit to ripen evenly with relatively high oil content, with rich, nutty, long-lasting flavor and aroma after cutting; the distinctive shape of the fruit and color of its meat with scarcity of fibers, fine texture and absence of sweetness, bitterness and soapiness; and relatively small size and distinctive shape of seed, substantially as shown and described.

MELVILLE M. GRAHAM.